US011364195B2

(12) United States Patent
Kumosani et al.

(10) Patent No.: US 11,364,195 B2
(45) Date of Patent: Jun. 21, 2022

(54) METHOD FOR ADMINISTERING LIPOSOMAL COMPOSITION

(71) Applicant: King Abdulaziz University, Jeddah (SA)

(72) Inventors: Taha Kumosani, Jeddah (SA); Elie Barbour, Jeddah (SA); Werner Krull, Jeddah (SA); Soonham Yaghmoor, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 17/505,119

(22) Filed: Oct. 19, 2021

(65) Prior Publication Data

US 2022/0105031 A1    Apr. 7, 2022

Related U.S. Application Data

(62) Division of application No. 17/210,769, filed on Mar. 24, 2021, now Pat. No. 11,160,752, which is a division of application No. 17/060,272, filed on Oct. 1, 2020, now Pat. No. 11,052,041.

(51) Int. Cl.
| | |
|---|---|
| *A61K 9/00* | (2006.01) |
| *A61K 9/127* | (2006.01) |
| *A61K 47/28* | (2006.01) |
| *A61K 9/107* | (2006.01) |
| *A61K 47/44* | (2017.01) |
| *A61K 47/10* | (2017.01) |
| *A61K 47/26* | (2006.01) |

(52) U.S. Cl.
CPC .......... *A61K 9/0043* (2013.01); *A61K 9/0073* (2013.01); *A61K 9/107* (2013.01); *A61K 9/127* (2013.01); *A61K 9/1277* (2013.01); *A61K 47/10* (2013.01); *A61K 47/26* (2013.01); *A61K 47/28* (2013.01); *A61K 47/44* (2013.01)

(58) Field of Classification Search
None
See application file for complete search history.

(56) References Cited

U.S. PATENT DOCUMENTS

| | | | |
|---|---|---|---|
| 6,004,560 A | 12/1999 | Hsu et al. | |
| 8,414,914 B2 | 4/2013 | Bromley et al. | |
| 9,610,314 B1 | 4/2017 | Krull et al. | |
| 9,801,842 B2 * | 10/2017 | Baker, Jr. | A61K 47/32 |
| 9,855,209 B1 | 1/2018 | Kumosani et al. | |
| 10,154,958 B1 | 12/2018 | Kumosani et al. | |
| 2001/0053775 A1 | 12/2001 | Seidel et al. | |
| 2005/0175683 A1 | 8/2005 | Zhang | |
| 2005/0281772 A1 | 12/2005 | Bromley | |
| 2009/0016961 A1 | 7/2009 | Yamazaki | |
| 2011/0104258 A1 * | 5/2011 | Pit | A61K 47/6911 424/450 |
| 2012/0251685 A1 * | 10/2012 | Wang-Nolan | C11B 5/0085 426/250 |
| 2013/0156868 A1 | 6/2013 | Schierstedt | |
| 2013/0156871 A1 | 6/2013 | Keller | |
| 2017/0354596 A1 | 12/2017 | Bonferoni | |

FOREIGN PATENT DOCUMENTS

| | | |
|---|---|---|
| CN | 1475204 A | 2/2004 |
| CN | 102258546 A | 11/2011 |
| CN | 110664689 A | 1/2020 |
| IN | 201400543 | 8/2016 |
| WO | WO 00/41709 A1 | 7/2000 |
| WO | WO 2018/024516 A1 | 2/2018 |

OTHER PUBLICATIONS

Marjan Javadi, et al., "Encapsulating Nanoemulsions Inside eLiposomes for Ultrasonic Drug Delivery", Langmuir, vol. 28, Sep. 18, 2012, pp. 14720-14729.
Sandy F. Van Vuuren, et al., "Encapsulation of Essential Oils within a Polymeric Liposomal Formulation for Enhancement of Antimicrobial Efficacy", Natural Product Communications (NPC), vol. 5, No. 9, 2010, pp. 1401-1408.
Changqi Sun, et al., "Physical Properties of Phosphatidylcholine Vesicles Containing Small Amount of Sodium Cholate and Consideration on the Initial Stage of Vesicle Solubilization", Chem. Pharm. Bull., vol. 50, No. 9, Sep. 2002, pp. 1145-1150.
Mirna Sherry, et al., "Essential oils encapsulated in liposomes: a review", Journal of Liposome Research, Jul. 2013, pp. 1-8.
Javadi et al (Langmuir, 2012, 28, 14720-14729). (Year: 2012).
Murthy et al. (International Journal of Nanomedicine, 2007, 2(2), 129-141) (Year: 2007).
Davis et al (Nature Reviews Drug Discovery, 7, 2008, 771) (Year: 2008).

* cited by examiner

*Primary Examiner* — Celeste A Roney
(74) *Attorney, Agent, or Firm* — Oblon, McClelland, Maier & Neustadt, L.L.P.

(57) ABSTRACT

The invention pertains to liposomes containing an oil-in-water emulsion of a selected combination of at least ten different essential plant oils produced with phospholipids found in human membranes and methods for treating respiratory diseases, disorders or conditions by administering the liposomes into the nose and respiratory system.

3 Claims, 1 Drawing Sheet

METHOD FOR ADMINISTERING LIPOSOMAL COMPOSITION

CROSS-REFERENCE TO RELATED APPLICATIONS

The present application is a Divisional of U.S. application Ser. No. 17/210,769, now allowed, having a filing date of Mar. 24, 2021, which is a Divisional of U.S. application Ser. No. 17/060,272, now U.S. Pat. No. 11,052,041, having a filing date of Oct. 1, 2020.

BACKGROUND OF THE INVENTION

Field of the Invention

The invention pertains to the fields of pharmacy and medicine specifically to a liposome composition containing a mixture of ten essential oils for treating respiratory diseases, disorders and conditions.

Description of Related Art

The administration of drugs into the nose is a widely used method for treating nasal congestion caused by allergies, colds or infections. The most common drugs nasally administered for these conditions are sympathomimetics including pseudoephedrine or phenylephrine which act as decongestants and produce local vasoconstriction. However, due to penetration of these locally applied drugs through the nasal mucosa into the general circulation, persons taking these drugs often experience undesirable side-effects including irritation of, or permanent damage to, nasal mucosal epithelium, respiratory disorders, central nervous system stimulation, trouble sleeping, heart palpitations, blood pressure elevation, and in some cases, such as in patients taking MAO inhibitors, potentially fatal hypertensive crises. Moreover, extended use of such drugs, especially topical decongestants, can lead to rhinitis medicamentosa a condition of drug dependence characterized by rebound nasal congestion, upon withdrawal of the decongestant. As a result, over-the-counter sprays with these types of active ingredients may actually lengthen the duration of common cold or sinusitis symptoms. Consequently, doctors often recommend a limited course of such drugs, such as use of a drug for no more than seven days, to minimize side-effects.

Other conventional medications and treatments for nasal congestion provide only minimal symptomatic relief and some also have undesirable side effects or other limitations. Over-the-counter medications containing antihistamines sometimes cause drowsiness and impair cognitive judgment so that driving an automobile or operating other power driven machinery can be dangerous. Inhaled corticosteroid nasal sprays provide some relief for allergic rhinitis but do not reduce inflammation caused by acute viral infections or inflammation associated with other forms of non-allergic rhinitis such as atrophic rhinitis, vasomotor rhinitis, or hormonally-induced vasomotor instability. Prolonged use of steroid sprays has also been associated with drying, cracking and bleeding of the nasal membranes.

Passive treatments, such as irrigation with isotonic saline mists, are also widely marketed for purposes of moisturizing the nose and relieving cold and allergy symptoms. Isotonic saline mists add moisture to the nose but provide little overall relief for congestion. For example, US Patent Publication US 20130156871 A1 discloses an isotonic nasal wash having a pH near 7.0 for alleviating dryness, rhinitis, and sinusitis. However, these more passive sprays and treatments have proved to be less than satisfactory at providing the relief sought by sufferers of colds or allergies or other nasal problems.

Various herbal products such as water extracts of various plants have been proposed for treatment of rhinitis. U.S. Pat. No. 6,004,560 A discloses a nasal spray for treating a fever or cold which is produced by boiling *Bupleurum Scorzonerifolium* Willd, *Radix lastidis Indigotica* and *Folium lastidis* in water and then mixing the boiled liquid with Vitamin C. WO 2000041709 A1 discloses a nasal spray based on a chamomile extract and xylometazoline which has a vasoconstrictive property. US Patent Publication US 20130156868 A1 describes a menthol-based nasal solution for providing a soothing effect on nasal mucosa. Barbour describes treatment of avians for various microbial diseases with a natural eucalyptus/peppermint essential oil-based preparation; Barbour et al., Int J. Appl. Res. in Veterinary Medicine 2011 Vol. 9 No 0.4 pp. 317-323. In addition, emulsions of some types of essential oils have been used to treat tooth decay, vaginal infections, and protozoan infection; see U.S. Pat. Nos. 9,855,209; 10,154,958 B1; 9,610,314B1; and WO/2018/024516A1. However, many herbal preparations are administered as a bolus and lack persistence in the nasal mucous requiring frequent repeated administration.

In view of the limitations and drawbacks of prior nasal preparations, the inventors sought to develop an emulsified composition comprising a select mixture of several natural oils that provides a broader spectrum of palliative, regenerative, antimicrobial and antiallergic properties, which can be formulated inside biocompatible liposomes for sustained release, and which avoids the side-effects of drugs such sympathomimetic and antihistamine drugs or those associated with administration of a large bolus of a single herbal ingredient.

BRIEF SUMMARY OF THE INVENTION

One aspect of the invention is directed to an emulsion of at least ten selected essential oils that is encapsulated in a liposome. The ten essential oils from oregano, thyme, eucalyptus, lime, frankincense, peppermint, lemon, ginger, sage, and lavender oils in combination provide a composition with broad antimicrobial, immunostimulatory and palliative properties. Moreover, the encapsulating liposome comprises compounds identical to, or biocompatible with, those found in human membranes and provides an excellent way to modulate the release of the ten emulsified oils.

Another aspect of the invention is a method for treating a nasal, sinus or respiratory disease, disorder, or condition by administering liposome nanoparticles containing the emulsion of a mixture of the ten essential oils. For example, a composition comprising the liposomes encapsulating the emulsion of ten essential oils can be delivered to the nostrils, sinuses or respiratory system as droplets or as a spray or wash to treat viral, bacterial or fungal infections, allergy, inflammation, dryness, or nasal or sinus congestion.

Another aspect of the invention is a method for producing the liposomal composition containing a water-in-oil emulsion of the ten essential oils by drying liposomal components on an inside of rotating container and slowing adding a material to be encapsulated in a liposome.

The liposome composition, typically in the form of nanoparticles, encapsulating the ten selected essential oils provides a valuable and safe addition to the presently marketed nasal products due to its wide range of antimicrobial, anti-inflammatory, pain killing, and anti-allergy activities and with its ability to moisturize, enhance and heal nasal, sinus and respiratory system membranes. This liposome composition also provides for sustained release of the essential oil components for an extended period of time and is produced using ingredients identical or biocompatible with nasal, sinus and respiratory system membranes. The encapsulation of the essential oil emulsion within the lipid bilayer of the liposome elongates the essential oil release time which is associated with direct delivery of the active ingredients into mucosal cells. This slower, prolonged release is associated with improved anti-inflammatory, antiviral, antibacterial, and anti-allergic effects, as well as with a moisturizing effect that maintains the integrity of the nasal epithelial layer.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings below.

DETAILED DESCRIPTION OF THE INVENTION

Figure 1:
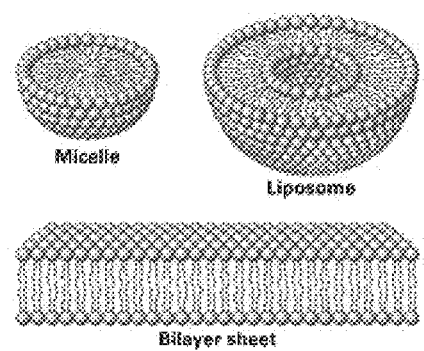
FIG. 1 depicts differences between micelles, liposomes and lipid bilayers.
Figure 2:
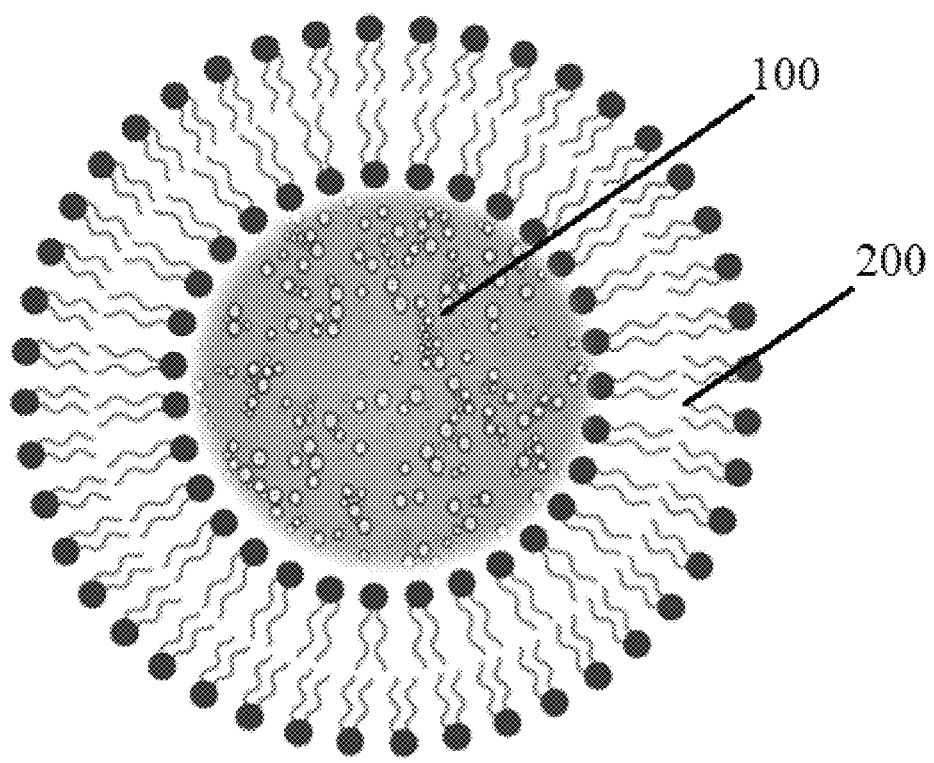
FIG. 2 depicts an embodiment of the liposome nanoparticles of the invention which contains a ten essential oil-in-water emulsion 100 within a liposomal lipid bilayer 200.

The technology disclosed herein provides a safe liposome-encapsulated oil-in-water emulsion of ten selected essential oils for treating nasal and respiratory disease, disorders and conditions. According to the World Health Organization, respiratory diseases are leading causes of death and disability in the world with annual deaths from respiratory ailments of about 650,000 people. The liposome composition disclosed herein, which contains ten select emulsified essential oils, can prevent upper respiratory symptoms and the infiltration of microbes from the upper to the lower part of the respiratory system. The prevention of infiltration of microbes from the upper to lower respiratory system is important for preventing or reducing the severity of diseases such those caused by SARS-COV-2, which binds to, and invades cells via, cellular receptors in the lower respiratory system. Each of the 10 essential oils was selected based on different mode of action due differences in active ingredients and concentrations of active ingredients.

The oil-in-water emulsion encapsulated within the liposome nanoparticles disclosed herein contains components having a documented record of safety. It is made from a mixture of ten organic essential oils which are oregano, thyme, eucalyptus, lime, frankincense, peppermint, lemon, ginger, sage, and lavender oils. Preferably, the essential oils are extracted from plants that are organically grown and harvested without pesticides or herbicides. The emulsion is made from a mixture of these ten oils in combination with one or more emulsifiers, preferably food or pharmaceutical grade emulsifiers. The liposomal membranes which encapsulate the emulsion of ten essential oils and the emulsifier can be selected to be of the same nature as molecules that form the membrane of human eukaryotic cells. For example, for preferred embodiments, the content of the engineered liposome nanoparticles includes phosphatidyl choline and cholesterol, ingredients that are naturally present in the membrane of all human eukaryotic cells; see Cooper G M, et al., Sinauer Associates. Cell membranes. 2000 Available from: hypertext transfer protocol secure://www.ncbi.nlm-.nih.gov/books/NBK9928/(incorporated by reference).

Essential oils are highly concentrated oils extracted from aromatic plants such as oregano and lavender. About 700 different types of plants contain useful essential oils, and there are several methods used to extract them—the most common of which is distillation, for example, water, water and steam or steam distillation. However, other methods include cold pressing, expeller pressing, and solvent extraction, such as with organic solvents or supercritical $CO_2$. Additional information about essential oils is incorporated by reference to ISO 4720:2009 which lists botanical names of plants used for the production of essential oils, together with the common names of the essential oils in English and French; and to ISO 4720:2009 which includes an alphabetical index of common names of essential oils in English and French.

High doses of a single oil can cause undesired side effects and are limited in antimicrobial spectrum and other functional activities. One advantage of including a blend of all ten essential oils is to use each oil in a lower concentration to avoid mucosal irritation and sneezing while benefiting from the cumulative healing power of the component oils. In addition, the spectrum of active components in each of the ten oils is very different thus their combination will provide a broad spectrum of molecules for prevention and treatment different infecting agents targeting the upper respiratory system and consequently prevent the infiltration of the infection to lower part of the respiratory system, mainly to lungs, thus controlling serious pneumonia conditions. Moreover, the ten essential oils disclosed herein exhibit different immunological and healing mechanisms on upper respiratory system ailments, including antiviral, antibacterial, anti-inflammatory, and immunomodulatory properties, stimulatory effects on cell-mediated immunity, anti-cough effects, anti-irritation effects, inhibition of microbial colonization, and antioxidant effects. Accordingly, ten different essential oils were selected for incorporation into the oil-in-water emulsion disclosed herein to reduce the concentration of each oil and avoid side effects of higher dosages of a single type of oil as well as to provide additive or synergistic antimicrobial and other therapeutic properties.

These ten essential oils are oregano, thyme, eucalyptus, lime, frankincense, peppermint, lemon, ginger, sage, and lavender oils. Typically, equal volumes (10 vol. %) of each oil are used to produce the mixture of essential oils used to produce an essential oil-in-water emulsion. In some embodiments, the amounts of each oil may range between 5, 10, 15 or 20 vol. % based on the total content of essential oils. The content of a mixture of the ten essential oils in the oil-in-water emulsion may be selected so as to provide a stable emulsion. In some embodiments, the mixed oil (all ten oils) ranges from 1 to 10 vol/vol % based on the total volume of the emulsion. Preferably, the mixed oil content ranges from about 1 to about 3 vol/vol. %.

The essential oil of oregano (Lamiaceae) was selected based on recognition of its antiviral and antibacterial properties. This oil may be obtained as described by, and incorporated by reference to, Bozin, et al., J. Agric. Food Chem. 54(5), 1822-1828, 2006.

The essential oil of thyme (*Thymus*) was selected for its anti-inflammatory and immunomodulatory properties. The oil may be obtained as described by, and incorporated by reference to, Fachini-Queiroz, et al., Evidence-Based Complement Alternat Med. 2012, 657026, 2012

Eucalyptus (*Eucalyptus*) essential oil was selected for its stimulatory effect on innate cell-mediated immune response, resulting in immunomodulation and antimicrobial effects. It may be acquired or produced as described by, and incorporated by reference to, Sarafino, et al., BMC Immunol. 9, 17, 2008.

Lime oil was selected for its wide spectrum-antimicrobial effect. This essential oil may be sourced as described by and incorporated by reference to Prabuseenivasan, S., et al., BMC Complement Altern Med. 6, 39, 2006.

Essential oil of frankincense (Boswellia). There are five main species of Boswellia that produce true frankincense with anti-cough properties. This essential oil may be acquired or produced as described by, and incorporated by reference to, Journal of Chromatography A. 1261, 158-63, 2012.

The essential oil of peppermint, was included in the ten essential oil mixture because spray application of peppermint oil was found to result in significant and immediate improvement in symptoms of upper respiratory ailments. This essential oil may be acquired or produced as described by, and incorporated by reference to, Ben-Arye, et al., Evidence Based Complement Alternat Med. 2011, 690346, 2011.

Lemon oil was selected based on its antimicrobial activity against respiratory pathogens like *Klebsiella pneumonia*. This essential oil may be acquired or produced as described by, and incorporated by reference to, Mose, et al., Arzneimittel-Forschung/Drug Research. 7, 687-692, 1957. Lemon essential oil is typically composed mainly of two major chemicals namely, (3-Pinene (25.44%), and Limonene (39.74%), and minor components of Linalool (2.16%), α-Terpineol (7.30%), linalyl acetate (3.01%), Acetate geranyl (3.03%), Nerolidol (6.91%), Acetate neryl (1.74%) and Farnesol (4.28%).

Ginger oil was selected on the bases of its anti-oxidative and anti-inflammatory effects. This essential oil may be acquired or produced as described by, and incorporated by reference to, Mashhadi, et al., Int J Prev Med. 4 (Suppl 1), S36-S42, 2013. One example of ginger rhizomes essential oil comprised sesquiterpenes (66.66%) and monoterpenes (17.28%), and lower concentrations of aliphatic compounds (13.58%). The predominant sesquiterpene is zingiberene (46.71%) followed by valencene (7.61%), β-funebrene (3.09%) and selina-4(14), 7(11)-diene (1.03%). The major monoterpenes are citronellyl n-butyrate (19.34%), β-phellandrene (3.70%), camphene (2.59%) and α-pinene (1.09%).

Essential oil of sage (*Salvia officinalis*) was selected for its antioxidant and antimicrobial activities. This essential oil may be acquired or produced as described by, and incorporated by reference to, Alizadeh, et al. Advances in Environmental Biology 1, 221-226, 2012. *Salvia officinalis* essential oil is composed of two major chemicals namely, cis-thujone (18-43 wt. %) and camphor (4.5-24.5 wt. %), associated with the following minor components of cineole (5.5-13 wt. %), humulene (0-12 wt. %), trans-thujone (3-8.5 wt. %), camphene (1.5-7 wt. %), pinene (1-6.5 wt. %), limonene (0.5-3 wt. %), bornyl acetate (maximum of 2.5 wt. %) and linalool (maximum of 1 wt. %).

The essential oil extracted from lavender (*Lavandula officinalis* Chaix.) showed strong antibacterial and antifungal properties. This essential oil may be acquired or produced as described by, and incorporated by reference to, Lodhia, et al. Indian Journal of Pharmaceutical Sciences, 71(2), 134-136, 2009. *Lavendula officinalis* essential oil has 78 compounds with two major constituents linalool and linalyl acetate at concentrations ranging between 10, 15, 20, 25, 30, 35 or 40 wt % and intermediate concentrations of geraniol, β-caryophyllene and lavandulyl acetate in a ranges between 3, 4, 5 and 6 wt % In one isolate of lavender oil the concentration of linalool is about 30.6 wt. % and the concentration of linalyl acetate is about 14.2 wt. % and the concentrations of geraniol about 5.3 wt. %, β-caryophyllene about 4.7%, and lavandulyl acetate about 4.4%.

These ten essential oils have been used by humans in folklore medicine and in foods for centuries with proven safety on human body, pending application in specific dose concentrations; Tisserand, R and Young, R. Essential Oil Safety. 2 ed. Edinburgh, UK: Churchill Livingstone, Elsevier, 2014 (incorporated by reference).

The essential oils disclosed herein are typically free of non-oily components found in so-called plant extracts which can include proteins and water-soluble components. A plant extract may be obtained from any of the plant parts including the leaves, pulp, seeds, stems, fruit and fruit seeds, as well as from the whole plant. The plant extract typically contains phytochemicals and/or metabolites that include, without limitation, alkaloids, flavonoids, saponins, carbohydrates, polysaccharides, terpenoids (e.g., monoterpenoids and sesquiterpenoids), steroids, sterols, phenols, tannins, anthraquinones, anthocyanins, amino acids, proteins, and vitamins.

In some separate embodiments, one, two, three, four or more of the ten essential oils may be omitted or one or more additional oils besides the ten specific essential oils described above may be incorporated into an oil-in-water emulsion that is encapsulated into liposomes of liposome nanoparticles. These include additional essential oils selected from one or more of agar oil, ajwain oil, angelica root oil, anise oil, asafoetida, Balsam of Peru, basil oil, bay oil, Bergamot oil, black pepper, birch oil, camphor, cannabis flower, caraway oil, cardamom seed oil, carrot seed oil, cedarwood oil, chamomile oil, calamus Root, cinnamon oil, cinnamon cassia, cistus species, citron, citronella oil, clary sage, clove leaf oil, coffee, coriander, costmary oil, costus root, cranberry seed oil, cubeb, cumin oil/black seed oil, cypress, cypriol, curry leaf, davana oil, dill oil, elecampane, fennel seed oil, fenugreek oil, fir, galangal, galbanum, geranium oil, goldenrod, grapefruit oil, henna oil, helichrysum, hickory nut oil, horseradish oil, hyssop, Idaho tansy, jasmine oil, juniper berry oil, *Laurus nobilis*, ledum, lemongrass, litsea cubeba oil, linaloe, mandarin, marjoram, melaleuca, Melissa oil, mentha arvensis oil/mint oil, moringa oil, mountain savory, mugwort oil, mustard oil, myrrh oil, myrtle, neem oil, Neem Tree Oil, neroli, orange oil, orris oil, Palo Santo, parsley oil, Patchouli oil, Perilla essential oil, peppermint oil, petitgrain, pine oil, Ravensara, Red Cedar, Roman Chamomile, rose oil, rosehip oil, rosewood oil, sandalwood oil, sassafras oil, savory oil, Schisandra oil, spearmint oil, spikenard, spruce, star anise oil, tangerine, tarragon oil, tea tree oil, Tsuga, turmeric, valerian, vetiver oil, Western Red Cedar, wintergreen, ylang-ylang, zedoary, or combinations thereof.

The essential oils described herein may be obtained from commercial sources or isolated from the corresponding plant sources which are preferably grown under organic conditions without pesticides or herbicides. Organic production of the plants from which the essential oils may be derived may be certified by Accredited Organic Certificates such as those granted by the USDA, see hypertext transfer protocol secure://www.ams.usda.gov/services/organic-certification/faq-becoming-certifying-agent (last accessed Jun. 5, 2020, incorporated by reference). One commercial source of USDA certified organic essential oils is Revive Essential Oils, 505 Montgomery Street, Suite 1025, San Francisco, Calif. 94111. Herbs may be harvested at a time of day when plant oil content is highest, preferably between 10 am to 11:00 am when essential oils are highly expressed in it. Essential oils may be isolated by various known techniques with steam distillation being a preferred method.

Emulsifiers which can be used to emulsify essential oils and water into an oil-in-water emulsion include polysorbates which are a class of emulsifiers often used in pharmaceutical, food, and cosmetic products. Polysorbates are oily liquids derived from ethoxylated sorbitan (a derivative of sorbitol) esterified with fatty acids. Some representative polysorbates are Polysorbate 20 (polyoxyethylene (20) sorbitan monolaurate), Polysorbate 40 (polyoxyethylene (20) sorbitan monopalmitate), Polysorbate 60 (polyoxyethylene (20) sorbitan monostearate) and Polysorbate 80 (polyoxyethylene (20) sorbitan monooleate). One preferred emulsifier for use in producing the oil-in-water emulsions disclosed herein is polyoxyethylene sorbitan monolaurate. Other food grade emulsifiers include lecithin, sodium phosphates and mono- and di-glycerides. In preferred embodiments, the emulsifier is an E20 food grade emulsifier (polyoxyethylene [20] sorbitan monolaurate; Tween 20®) which is incorporated into the essential oil-in-water emulsion in amounts of 0.1 to 8.0 vol/vol %, and preferably between 1.6-2.0 vol/vol %.

A food grade emulsifier, such as polyoxyethylene sorbitan ester like polyoxyethylene sorbitan monolaurate (Tween 20®), is able to create a homogeneous dispersion of the components present in the ten essential oils and help standardize the antimicrobial, anti-inflammatory, anti-allergy, anti-pain effects of the mixed oils in the emulsion when contacted with different parts of the nasal or respiratory system. Such an emulsifier is acceptable as a food additive and may be incorporated into the liposome compositions disclosed herein in amounts of 0.1, 0.2, 0.5, 1, 2, 5 to 8.0 vol./vol %, and preferably between 1.6-1.8-2.0 vol./vol %, is safe based on acceptable daily intake of up to 25 mg/day of such food grade emulsifiers in foods suggested by WHO in 1974.

An emulsion is a fluid system in which liquid droplets are dispersed in a liquid. One component of the liposome composition disclosed herein is an essential oil-in-water emulsion which is encapsulated in liposomes. Oil droplets in the dispersed phase of the essential oil-in-water emulsion disclosed herein may range from 10, 50 100, 200, 500, <1,000 nm (nanoemulsion) or 1000 nm (1 µm), 2, 5, 10, 20, 50 to 100 µm (macroemulsion). Preferably, the average diameters of oil droplets of the essential oil-in-water emulsions are less than 1,000 nm. The droplet size in the essential oil-in-water emulsion may be increased or decreased to modify the pharmacokinetic rate of release of essential oils when administered to a subject. In some embodiments, the nanoemulsion is stable at room temperature for at least 3, 6, 9 or 12 months. In another embodiment, the nanoemulsion releases about 20, 30, 40, 50, 60 or 70 wt % of the essential oils over a period of 4, 6, 8, 10, or 12 hours when applied to the nostrils or to the nasal mucosa.

In a preferred embodiment, the essential oil-in-water emulsion is passed through a colloidal mill at fine stator gap to create a nanoemulsion with droplet diameter of 3.0 millimicron (3.0/1000 of a micron), resulting in stable emulsion encapsulated in liposome micelles for a period of one year, and following application into the nostrils, release of around 50% of the essential oil over a period of 12 hrs, following the application in the nostrils.

Antioxidants and vitamins. In some embodiments, the essential oil-in-water emulsion may contain additional ingredients such as antioxidants, vitamins, minerals or pH buffers. Antioxidants include ascorbyl palmitate, BHT, ascorbic acid, sodium ascorbate, monosterol citrate, tocopherols, propyl gallate, tertiary butylhydroquinone (TBHQ), butylated hydroxyanisole (BHA), vitamin E, or any combination thereof. Antioxidants can stabilize oils in an emulsion and prevent their oxidation.

Fat soluble vitamins including vitamins A, C (as ascorbyl palmitate), D and K may optionally be incorporated into the oil-in-water emulsion disclosed herein. Vitamin A plays a major role in keeping your respiratory, intestinal and urinary tract surface linings healthy. This nutrient assists in keeping your mucous membranes and skin properly nourished to function as a barrier against harmful viruses and bacteria. Vitamin C is necessary for healthy mucosa and helps reduce inflammation. Vitamin C as ascorbyl palmitate is fat soluble and can absorbed into the cell membrane where ascorbic acid cannot reach. Vitamin D supports the normal function of the immune system, can benefit the nasal mucosa which protects from viral respiratory infections and provides protection against allergies, such as mold allergies. Vitamin D deficiency is associated with chronic rhinosinusitis (CRS) a chronic inflammatory disease of the sinuses and nasal mucosa sometimes characterized by polyposis. Vitamin K is a group of structurally similar, fat-soluble vitamins found in foods and in dietary supplements. The human body requires vitamin K for complete synthesis of certain proteins that are needed for blood coagulation or for controlling binding of calcium in bones and other tissues. It has a role in protecting fine bony structures in the nasal cavity, such as delicate paranasal sinus bones, from damage from sinus infections and other nasal disorders. Fat soluble vitamins may be incorporated in the essential-oil-in-water emulsion in an amount from about 0.001 to about 0.05% by weight.

In some embodiments, the aqueous phase of an oil-in-water emulsion or an aqueous phase containing liposomal nanoparticles may contain mineral components such as zinc (e.g. zinc salts like zinc citrate) or copper (e.g. copper salts like copper gluconate). Zinc and copper are trace minerals that have roles in maintaining the immune system and in diseases plays in which oxidant stress is elevated, such as certain nasal and respiratory diseases. These metals may be present in the liposome composition or in the essential-oil-in-water emulsion in an amount from about 0.001 to about 0.01% by weight.

In some embodiments, the aqueous phase of an oil-in-water emulsion or an aqueous phase containing liposomes or liposome nanoparticles will contain a buffer. One skilled in the pharmaceutical or medical arts may select an appropriate buffer. Some representative buffers include dibasic sodium phosphate, monobasic sodium phosphate, citric acid, sodium citrate, acetic acid, sodium acetate, boric acid, sodium carbonate, sodium borate, hydrochloric acid and sodium hydroxide. The oil-in-water emulsion may be formulated at different pHs depending on the type of disease, disorder or condition being treated, for example, it may have a pH of <5, 5, 5.5, 6, 6.5, 7, 7.5, 8 or >8. In some embodiments, the oil-in-water emulsion may be adjusted to, or buffered at the nasal mucosal pH which approximately 5.5-6.5. Often in rhinitis nasal pH increases to pH 7.2-8.3 and the pH of the composition or emulsion may be adjusted to fall within this range, for example, during healing of nasal irritation or damage, or may be adjusted to bring the nasal pH down to a more normal value. The oil-in-water emulsion or an aqueous phase containing the liposome nanoparticles may contain an aqueous phase that is isotonic (e.g., about 0.9% salt) with the nasal mucosa. However, in some embodiments, the aqueous phase may be hypo- and hypertonic.

A liposome is a spherical vesicle having at least one lipid bilayer, see FIG. 1. The liposome can be used as a vehicle for administration of nutrients and pharmaceutical drugs. Liposomes can be prepared by disrupting biological membranes (such as by sonication). Preferably, the liposomes disclosed herein have an average diameter of less than 1, 2, or 3 μm and are made by a method comprising drying liposomal components on an inside of rotating container and slowing adding a material to be encapsulated in the liposome, specifically, an oil-in-water emulsion of ten essential oils as disclosed herein. Liposomes are typically composed of phospholipids, especially phosphatidylcholine, but may also include other lipids, such as egg phosphatidylethanolamine, so long as they are compatible with lipid bilayer structure. In some embodiments, the phospholipids components of the liposomes are phosphatidylcholines, phosphatidylethanolamines, phosphatidylserines, phosphatidylglycerols, phosphatidylinositols, phosphatidic acids, mixed chain phospholipids, lysophospholipids, hydrogenated phospholipids, partially hydrogenated phospholipids, and mixtures thereof.

Preferably, the components used to make the liposomes are selected to be substantially identical to components present in the human body, such as cells forming the epithelial tissue of the respiratory system.

The engineered liposome nanoparticles disclosed herein are preferably similar in structure to the bi-lipid layer of phospholipids that form the membrane of the targeted mucosal eukaryote cells, thus allowing for fusion of the engineered liposome with the epithelial cells in the respiratory system, and by that allowing for direct delivery of the encapsulated essential oils to act on intracellular infecting microbes and other phagocytized organisms, and on extracellular colonies of microbes present on the surface of the epithelial cells.

Preferably, the liposome nanoparticles disclosed herein lack any inclusion of a chemical structure, such as a peptide, protein, lipoprotein, glycoproteins, polysaccharides, mucoadhesive proteins, or other components that induce injurious immune reactions via activation or recognition by local immune cells present in the mucosal layer of the respiratory system. It can exclude milk, serum, mucosal, pulmonary, epidermal, and other cellular proteins. Thus it will be substantially free of antigens creating injuries to the mucosal layer contacted with the liposome nanoparticles. This avoids many problems associated with administration of non-self antigenic proteins or carbohydrates as well as denatured or altered autologous proteins or carbohydrates, and helps avoid undesirable immunological or physiological reactions to these liposome components when they are administered to a subject.

In one embodiment, the liposome nanoparticles further comprise polyethylene glycol (PEG) to improve the pharmacokinetics by providing a protective, steric barrier against interactions with plasma proteins and cells. Other emulsion or liposome stabilizers or preservatives may also be included. Preferably, the liposomal nanoparticles are stable for a period of at least 0.25, 0.5, 0.75, 1, 1.5 or 2 years, showing no more than 0.1, 0.2, 0.5 or 1 wt. % separation, and more preferably, no split or separation of its different aqueous and lipid phases.

Liposome nanoparticle composition. Typically at least 90 or 95 wt. % of the essential oil emulsion is encapsulated and the small amount of unencapsulated essential oil emulsion typically does not produce irritation or injury to the nostrils or sinuses. The composition may contain about 1, 2, 3, 4, 5 to 10 wt % of surplus emulsified essential oils, which have not been encapsulated in liposomal nanoparticles and thus fill space between and among the liposomal particles.

In another embodiment, the liposomal nanoparticles disclosed herein containing the ten emulsified essential oils may be suspended in an aqueous phase which may contain <0.1, 0.1, 0.2, 0.5, 1, 2, 5, 10, 20, 30, 40, 50, 60, 70, 80, 90, 95 or >95% liposomes based on the volume or weight of the composition.

Preferably, the composition comprising the liposomal nanoparticles as disclosed herein is in a liquid form rather than in a form of an emulsion, cream, lotion, gel, ointment, emollient, wax, or other semisolid or semiliquid form. The composition may have a viscosity ranging from 0.5, 0.6, 0.7, 0.8, 0.9, 1, 1.1, 1.2, 1.3, 1.4, 1.5, 1.6, 1.7, 1.8, 1.9, 2.0 or >2.0 mPa·s.

The liposome nanoparticle composition of the invention is locally or topically applied and is formulated from ten natural essential oils and omits conventional drugs and medicines such as sympathomimetic and antihistamine drugs. It may be inhaled or washed over a nasal membrane. The ten oils as well as the emulsifier and liposomal components have been previously safely used in many products. Thus, its production and sale would not be constrained by many regulations or guidelines pertaining to systemically administered drugs.

Method of administering composition comprising the liposome nanoparticles loaded with an essential oil-in-water emulsion of ten essential oils. The composition may be nasally administered to a subject in an amount sufficient to reduce the sinus or respiratory irritations such as severity of sinus headache associated with inflamed or congested turbinates or other nasal tissues or for symptomatic relief of sinus headache and nasal congestion. It may also be administered or relieving symptoms of sinusidal pain associated with coryza, nasal congestion, allergic rhinitis and sinusitis by the direct application to affected nasal mucosa.

The liposome nanoparticle composition may be administered to treat a patient infected by, or at risk of infection by, viruses such as rhinovirus, respiratory syncytial virus, human parainfluenza viruses, adenovirus, human coronaviruses, human metapneumovirus and other respiratory viruses.

It may be administered to a patient infected by, or at risk of infection by, bacteria such as alpha hemolytic streptococci, beta hemolytic streptococci, *Branhamella catarrhalis*, Diptheroids, *Haemophilis influenzae* (beta-lactamase positive and negative), *Moraxella* species, *Pseudomonas aeruginosa, Pseudomonas maltophilia, Serratia marcescens, Staphylococcus aureus, Streptococcus pneumonia* and other respiratory bacteria.

It may be administered to a patient infected by, or at risk of infection by, fungi such as *Aspergillus, Mucor* and *Candida albicans, Fusarium, Curvularia, Cryptococcus, Coccidioides,* and *Histoplasma.*

A dosage regimen may be selected or recommended by a medical professional or self-selected. In a preferred embodiment, two drops (about 100 microliters) of a composition comprising the liposome nanoparticles as disclosed herein is administered to each nostril once or twice a day during the early signs of either dyspnea, sinus pressure, throat irritation and soreness, stuffy nose due to nasal congestion, resulting from infection by microbes, allergy, or apparent inflammation. An amount of the composition may be selected by a medical professional or patient based on the underlying condition, size, age or other patient factors. Typically, an amount of liposome composition used per application is about 2 drops (100 microliters) of the liposomal nanoparticle composition per nostril.

A total amount of lipids and other liposome components such as detergent sufficient to encapsulate at least 80, 85, 90, 95 or >95% of the essential-oil-in-water emulsion may be used to produce the liposome composition disclosed herein. Preferably, the liposomal nanoparticle composition is prepared by incorporating 0.11 to 0.13 g of total lipids into a total volume of 100 ml while respecting a molar ratio of phosphatidyl choline to cholesterol of 7:3, and including a sodium cholate detergent for dissolving the lipids at a molar ratio of phosphatidyl choline to sodium cholate of 0.52. In other embodiments, the ratio of phosphatidyl choline to cholesterol may range from 5:3, 6:3, 7:3, 8:3, to 9:3 and the of ratio phosphatidyl choline to sodium cholate from 0.42, 0.52 to 0.62.

The mixture of liposome components is then dialyzed through a membrane of 10,000 cut point for a period of 3 hrs against 500 ml of phosphate-buffered saline of pH 7.0 to remove excess detergent. This preparation will be dried on an inner wall of a 50 ml round flask attached to a rotary vapor apparatus. The 100 ml essential oil emulsion is added slowly to the dried film on the rotating flask to encapsulate it within the liposomal particles. Smaller diameter liposomes of less or equal to 3 micrometer diameter, suitable for delivery to the upper and lower respiratory passages, are obtained by sonication with non-continuous pulse, a 50% duty cycle, and a 20 Khz ultrasonic vibration. The complete formulation is filled into sterilized bottles, labeled regulatory or proprietary information, and packaged for shipping.

Devices for delivering the liposome nanoparticle composition disclosed herein to the nose or respiratory tract may be those that are conventionally used in the art for such purposes. These include inhalers, nebulizers, nose drop bottles, neti pot or other lavage device, dropper bottles or any other device suitable for delivering the liposome nanoparticle composition to the nose, sinuses, bronchia, or lungs. The concentration of liposomes in a composition for administration may be selected based on the needs of the patient, the type of disease, disorder or condition being treated, as well as on the mode of delivery. In some embodiments, the dosage of a composition comprising the liposome nanoparticles loaded with the emulsified essential oils may range from 50, 100, 200, 500, 1,000 or >1,000 μL. A dosage may be given as needed for symptomatic relief or given 1, 2, 3, 4, 5, 6 or more times per day for a period of <1, 2, 3, 4, 5, 6 or >6 weeks. A given dose may contain <1, 1, 2, 3, 4, 5, 6, 7, 8, 9, 10, 20 or >20 μL of the emulsion of ten essential oils or 0.1, 0.2, 0.3, 0.4, 0.5, 0.6, 0.7, 0.8, 0.9, 1, 2 or >2 μL of the essential oils per se per dose.

Additional embodiments of this technology include, but are not limited to the following.

One embodiment of the invention is a composition comprising, consisting essentially of, or consisting of liposomes containing an oil-in-water emulsion comprising at least one pharmaceutically acceptable emulsifier and a mixture of essential plant oils, wherein said mixture comprises oils of oregano, thyme, eucalyptus, lime, frankincense, peppermint, lemon, ginger, sage, and lavender. Preferably, the essential oils consist of those of oregano, thyme, eucalyptus, lime, frankincense, peppermint, lemon, ginger, sage, and lavender, wherein said oil-in-water emulsion is in a form of liposomes.

Typically, the liposome composition, or liposome nanoparticle composition, is in liquid form, such as in droplet form or in a form of a wash though in some embodiments it may be applied in a form of a gel or other viscous preparation or in a desiccated or concentrated form for reconstitution prior to use.

Advantageously, the emulsifier may be selected to be a food grade emulsifier that is already used in foods and pharmaceuticals and which has been demonstrated to be safe, such as polyoxyethylene sorbitan monolaurate. The content of the emulsifier is selected to provide a uniform emulsion of the ten essential oils. In some embodiments, the content ranges from 0.5, 1, 1.5, 2, 2.5, 3, 3.5, 4, 4.5, 5, 5, 7, or 8 vol/vol % based on the total volume of the essential oils, emulsifier and water.

The liposomes or liposomal membranes which encapsulate the emulsion of ten essential oils may be produced from components known in the art and preferably from components natural to or found in the human body, such as phosphatidyl choline and cholesterol.

Liposomes typically comprise a detergent, such as a sodium cholate detergent. Excess detergent may be removed, for example, by dialysis against saline, PBS or another physiologically acceptable buffer, after formation or isolation of the liposomes.

In one embodiment, the liposomes comprise phosphatidyl choline, cholesterol, and a sodium cholate detergent; wherein the molar ratio of phosphatidyl choline to cholesterol ranges from 8:3 to 6:3 and wherein the molar ratio of phosphatidyl choline to sodium cholate ranges from 0.4 to 0.6. The liposomes in some embodiments may further comprise at least one phosphoglyceride naturally found in human membranes, other than phosphatidyl choline, such as phosphatidyl ethanolamine, phosphatidyl inositol, phosphatidyl serine, or diphosphatidyl glycerol.

Typically, the liposome composition comprises liposomal nanoparticles no more than 3 microns in average diameter, such as 0.5, 1, 1.5, 2, 2.5, 3 microns in diameter. In other embodiments, the liposomal particles may exceed 3 microns in average diameter.

Preferably, the liposome composition has a pH ranging from 5, 5.5, 6, 6.5, 7, 7.5 to 8.

Advantageously the liposome composition disclosed herein containing the ten emulsified essential oils can be formulated to be free of irritants and artificial drugs such as sympathomimetic drugs, antihistamine drugs, corticosteroids, and mast cell stabilizing drugs, as well as proteins and other potentially immunogenic components such as carbohydrates, glycoproteins, and lipoproteins, especially those exogenous to the human body. In one embodiment, the liposomes may further comprise polyethylene glycol or PEG, a stabilizing agent to prevent degradation of the liposomes during storage, or a preservative, such as an antioxidant that prevents oxidation of the lipid and other components of the liposome.

Another embodiment of the invention is directed to a method for making the liposomal composition described herein containing an emulsion of ten essential oils that comprises mixing essential oils of oregano, thyme, eucalyptus, lime, frankincense, peppermint, lemon, ginger, sage, and lavender to form a mixture of essential oils, incorporating an emulsifier and water into the mixture of essential oils to form an essential oil-in-water emulsion, loading the essential oil-in-water emulsion into liposomes. The content of essential oils, emulsifier, and liposome components may be selected based on the ranges disclosed herein for these compositions and ingredients.

Preferably, this method uses polyoxyethylene sorbitan monolaurate as the emulsifier in an amount ranging from 1 to 3 vol. % based on a total volume of the oil-in-water emulsion and the liposome components comprise phosphatidyl choline, cholesterol, and a sodium cholate detergent; wherein the molar ratio of phosphatidyl choline to cholesterol ranges from 8:3 to 6:3 and wherein the molar ratio of phosphatidyl choline to sodium cholate ranges from 0.4 to 0.6; and wherein said loading comprises producing a dry film of the liposome components on an inner surface of a rotating container, slowly adding the essential oil-in-water emulsion to the rotating container thereby forming liposomes containing the emulsion, and reducing the average diameters of the formed liposomes to 3 μm or less.

Another embodiment of the invention is directed to a method for treating a respiratory disease, disorder or condition comprising administering the liposome composition disclosed herein into the nose or respiratory tissues of a subject in need thereof.

The composition is in a dispensable form, typically, in liquid form for dispensing as a droplet or spray. However, in some embodiments in may be in a more viscous, semisolid or semiliquid form such as in the form of a gel.

This method may be used to treat a subject, preferably a human subject, but in some cases other mammalian or avian subjects, having or at risk of acquiring a respiratory disease, disorder or condition. In some embodiments of this method the respiratory disease, disorder or condition is a nasal or respiratory infection with a virus, bacterium, or fungi, in other embodiments it is allergy, dryness, or irritation.

EXAMPLES

Example 1A. Production of Liposomes Containing an Essential Oil-In-Water Emulsion (Small Prep)

An emulsion of the ten essential oils, food grade emulsifier and water is prepared from 0.2 vol. % of each of the ten essential oils of oregano oil, thyme oil, eucalyptus oil, lime oil, frankincense oil, peppermint oil, lemon oil, ginger oil, sage oil and lavender oil, 1.6 v/v % of the Tween 20 emulsifier, and 96.4 vol/vol. % water. These amounts are safe based on an acceptable daily intake of up to 25 mg/day as suggested by WHO in 1974. The food grade emulsifier, polyoxyethylene sorbitan monooleate monolaurate, is able to create a homogeneous dispersion of all active ingredients present in the essential oil blend, resulting in similar antimicrobial, anti-inflammatory, anti-allergy, anti-pain effect at each point of the respiratory tissues.

The preparation of the liposomal nanoparticles for a total volume of 100 ml incorporates total lipids of 0.11-0.13 g, while respecting a molar ratio of phosphatidyl choline to cholesterol of 7:3, and including a sodium cholate detergent for dissolving the lipids at a molar ratio of phosphatidyl choline to sodium cholate of 0.52. Dialysis is performed through a membrane of 10,000 cut point for a period of 3 hrs against 500 ml of phosphate-buffered saline of pH 7.0 to remove the excess detergent. This preparation is dried on the inner wall of a 50 ml round flask attached to a rotary vapor apparatus.

The 100 ml essential oil emulsion is added slowly to the dried film on the rotating flask to encapsulate it within the liposomal particles. Smaller diameter liposomes of less or equal to 3 micrometer diameter are obtained by sonication with non-continuous pulse, a 50% duty cycle, and a 20 Khz ultrasonic vibration, to ensure the delivery of the nasal preparation to upper and lower respiratory passages. The liposome nanoparticle composition is filled in sterilized bottles or suitable dispensing devices, labeled, and packaged for shipping.

Example 1B. Production of Liposomes Containing an Essential Oil-In-Water Emulsion (Large Prep)

Two hundred milliliters of each of oregano oil, thyme oil, eucalyptus oil, lime oil, frankincense oil, peppermint oil, lemon oil, ginger oil, sage oil, and lavender oil were mixed to form 2 liters of blended essential oils.

Then, 1.6 L of polyoxyethylene sorbitan monolaurate (E20) was incorporated into the 2 liters of mixed oils form an oil phase. The polyoxyethylene sorbitan monolaurate (E20) emulsifier is used for creating an essential oil blend-in-water emulsion, is a food grade, used in many foods, with proven safety on human health. Fruijtier-Polloth, Toxicology. 214, 1-38, 2005, incorporated by reference. Water (96.4 L) is slowly added with gentle propeller mixing to the oil phase to form a final volume of 100 L on an essential oil-in-water emulsion. Thus, the volume percent composition of the organic essential oil blend-in-water emulsion is: water/oregano oil/thyme oil/eucalyptus oil/lime oil/frankincense oil/peppermint oil/lemon oil/ginger oil/sage oil/lavender oil/E20 emulsifier corresponding to 96.4/0.2/0.2/0.2/0.2/0.2/0.2/0.2/0.2/0.2/0.2/1.6 (V/V).

The water is added slowly to the oil phase, while mixing gently, using a propeller mixer, to form 100 liters an essential oil-in-water emulsion.

Separately from the production of the essential oil-in-water emulsion, a liposome-forming composition is prepared from phosphatidyl choline, cholesterol and sodium cholate and has a total lipid content ranging from 110 to 130 g. These ingredients are mixed in the following ratios to form the composition: (i) a ratio of 7:3 of phosphatidyl choline to cholesterol, (ii) ratio of 0.52 of phosphatidyl choline to sodium cholate detergent.

This liposome-forming composition was then dissolved in one liter of sterile phosphate buffered saline (PBS) and was dialyzed against PBS using a 10,000 cut point membrane.

The dialyzed composition was then dried on a sterile, clean inner surface of a rotating container with capacity of 150 liters to produce a dried film of liposome-forming lipids on the inner surface.

The 100 liters of essential oil blend-in-water emulsion was slowly added over the dried film of liposome-forming lipids, while the spherical vessel was rotating to form the liposomes that encapsulate the essential oil-in-water emulsion within its bilayers.

The resulting liposomes in the 100 L preparation are reduced to a diameter of 3 μm or less using a colloidal mill set at a stator gap of 3 μm.

Both the rotor of the mixer and stator of the colloidal mill have smooth surfaces. The rpm of the mixer and colloidal mill may range between 300-3000 rpm; preferably the mill is operated at about 1,000 rpm.

Typically the final volume of the liposome composition is approximately the same as that of the oil-in-water emulsion used to make it because the thin dried layer of liposomal forming materials on the wall of the rotating vessel adds a negligible volume. Thus, after milling and encapsulation within the liposome the volume will be about 100 ml. Preferably, it is not necessary to concentrate the liposomal content of the prepared composition before use. The composition may be formulated with a known content of liposome-forming materials and dried on the inside wall of the rotating flask and a known amount of essential oil-in-water emulsion is slowly added to the flask to be encapsulated within the liposome vesicles and is suspended in the aqueous environment forming its bilayer structure. In other embodiments, the concentration of liposomes produces as disclosed herein may be adjusted either by concentration of the liposomes or by dilution, for example, by admixture with a pharmaceutically acceptable carrier or other active ingredients to dilute the concentration of liposomes to 5, 10, 20, 30, 40, 50, 60, 70, 80, 90 or <100% of their original concentration.

Example 2. Evaluation of Antibacterial Properties of Liposomes Containing Essential Oil-In-Water Emulsion The nasal mucosa of twenty people, 10 men and 10 women 30-35 years old, are sampled using nasal swabs before and after treatment with liposomes containing the essential oil-in-water emulsion as described in Example 1. Samples are taken 0 hours (control) and at 6 and 12 hours after treatment with 2 drops per nostril (0.1 ml/nostril) of the liposomes.

Each sample is suspended in sterile saline solution, serially diluted, plated, and incubated aerobically. The bacterial count on the plates was recorded and compared to control values, see Table 1 below.

TABLE 1

Mean bacterial count in nasal swabs collected before treatment with nasal preparation and at three times after treatment Mean Bacterial count/nasal swab

| Gender | Before Treatment | After Treatment with Nasal Preparation (Hrs) | | |
|---|---|---|---|---|
| | | 1 | 6 | 12 |
| Male | $(3.0 \times 10^4)^{a,1}$ | $(5.0 \times 10^3)^{a,2}$ | $(2.7 \times 10^2)^{a,3}$ | $(5.3 \times 10)^{a,4}$ |
| Female | $(2.2 \times 10^4)^{a,1}$ | $(3.4 \times 10^3)^{a,2}$ | $(1.8 \times 10)^{a,3}$ | $(4.2 \times 10)^{a,4}$ |

$^a$Means in a column followed by the same alphabet superscript are insignificantly different at $P > 0.05$.
[1-4]Means in a row followed by different Arabic numerical superscripts are significantly different ($P < 0.05$). Means of the counts at different times were compared statistically by one way ANOVA followed by conservative Tukey's Test, including comparison of each of the two genders at different times.

Example 3. Targeted Reduction of Nasal Congestion at Different Points in Time in Hospitalized Patients Having Severe Respiratory Symptoms after Administration of Liposomes Containing Essential Oil-In-Water Emulsion The degree of nasal congestion was evaluated by a medical professional and the amount of nasal secretions over a 1 minute period is measured in ten patients experiencing rhinitis or nasal congestion. Patients were then administered 2 drops per nostril (0.1 ml/nostril) of the liposome preparation as described by Example 2. The degree of nasal congestion and amount of nasal secretions were measured at 1, 6 and 12 hours after administration of the liposomes and compared to pre-treatment values (Table 2). Nasal congestion was evaluated by a score of 0 or 3, where 0 indicated no improvement, while 3 was the maximum improvement observed. A score 3 was confidently given by when the person is had no more dyspnea (difficulty or labored breathing). Results are shown by Table 2 and show progressive improvement compared to pretreatment values over a period of 12 hours.

| Mean Score of nasal congestion (score of 0 or 3) | | | |
|---|---|---|---|
| Before treatment | After Treatment in real time (hrs) | | |
| | 1 hr | 6 hrs | 12 hrs |
| $0^1$ | $1.2^2$ | $1.8^3$ | $2.4^4$ |

[1-4]Means in a row followed by different Arabic numerical superscripts are significantly different ($P < 0.05$). Means of the scores at different times were compared statistically by One Way ANOVA followed by conservative Tukey's Test.

Example 4. Evaluation of Antibacterial and Antiviral Properties of Liposomes Containing Essential Oil-In-Water Emulsion Suspensions of viable *Streptococcus* spp. and *Klebsiella pneumonia* bacteria and suspensions of rhinovirus and influenza H9B2 subtype are prepared.

Titrated amounts of the liposome preparation described in Example 1 are added to In vitro susceptibility testing of the invented preparation against gram positive and gram negative bacteria, and against Rhino and influenza viruses.

The essential oil blend-in-water emulsion is put in contact for different times (0, 5, 15, 30 minutes) against *streptococcus* spp. (gram positive), *Klebsiella pneumonia* (gram negative), rhinovirus, and influenza H9N2 subtype. The inactivation of the 4 test organisms after each contact time is recorded.

Example 5. Ames Testing Liposomal Preparation

To evaluate the safety of the liposomal preparation described in Example 1, the Ames test is performed according to the procedure described by, and incorporated by reference to, Ames et al, *Carcinogens are mutagens: their detection and classification*. Environ Health Perspect. 1973 Dec.; 6:115-8; Mortelmans and Zeiger, *The Ames Salmonella/microsome mutagenicity assay*. Mutat Res. 2000 Nov. 20; 455(1-2):29-60.

Briefly, the test organism *Salmonella enterica* subsp. *Enterica* serovar *typhimurium* (ATCC® 29629-Strain Designations: TA 1535), an auxotrophic mutant, is provided by ATCC, Manassas, USA. This auxotrophic isolate has a mutation in its DNA which prevents it from producing histidine and thus requires histidine for its growth.

Potentially mutagenic substances are identified by contacting them with this auxotrophic mutant and measuring the frequency of mutations that restore the ability of this auxotroph to grown a medium not containing histidine.

The liposomal preparation described by Example 1 is Ames tested by incorporating it at four different concentrations: ¹⁄₁₀₀X, 1X, 1.5X, and 2X, where X is the concentration of the final liposome preparation applied into a histidine-free medium used for the Ames test. Each concentration (X) is added to double strength histidine-free medium in 1:1 ratio. Double strength medium was used to avoid its dilution due to addition of an invented preparation in 1:1 ratio.

A negative control culture that is not exposed to the liposomal preparation and positive control cultures containing 20 or 200 nmole concentrations of a known mutagenic compound, ethidium bromide, are also made.

Consequently, the auxotrophic *S. typhimurium* is cultured in triplicate onto the solid culture media having the four different concentrations of liposomes and in the negative (no liposomes) and positive control media. The bacterium is spread over these media with small amount of histidine that helps in initiation of the growth. However, once this amino acid is depleted only cells mutated to produce histidine by the liposome preparation described by Example 1 continue their growth.

A degree of mutagenicity of the liposome preparation is determined by comparison of the number of colonies appearing on the negative and positive controls and the number of colonies on the solid medium containing different concentrations of the liposome preparation containing the essential oil-in-water emulsion of Example 1.

Results indicating nonsignificant differences in counts between negative control and test plates comprising the 1/100X, 1X, 1.5X and 2X concentrations of the liposome preparation indicate that the preparation is non-mutagenic as shown by the Ames test. A positive result with a significant increase in colony counts on the positive control plates incorporating 20 and 200 nmol ethidium bromide is expected.

Terminology used herein is for the purpose of describing particular embodiments only and is not intended to be limiting of the invention.

As used herein, the singular forms "a", "an" and "the" are intended to include the plural forms as well, unless the context clearly indicates otherwise.

As used herein, the term "and/or" includes any and all combinations of one or more of the associated listed items and may be abbreviated as "/".

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all subranges subsumed therein.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it also describes subranges for Parameter X including 1-9, 1-8, 1-7, 2-9, 2-8, 2-7, 3-9, 3-8, 3-7, 2-8, 3-7, 4-6, or 7-10, 8-10 or 9-10 as mere examples. A range encompasses its endpoints as well as values inside of an endpoint, for example, the range 0-5 includes 0, >0, 1, 2, 3, 4, <5 and 5.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

The invention claimed is:

1. A method for administering a liposomal composition into the nose or respiratory tissues of a subject in need thereof, comprising:
spraying droplets of the liposomal composition in a nostril of the subject,
wherein the liposomal composition contains liposomal particles containing an oil-in-water emulsion, said oil-in-water emulsion consisting of water, a polyoxyethylene sorbitan ester in an amount ranging from 1 to 3 vol. % based on a total volume of the liposomal particle essential oil-in-water emulsion and a mixture of essential plant oils in an amount ranging from 1 to 3 vol. % based on a total volume of the liposomal particle essential oil-in-water emulsion and that is free of water soluble components other than the polyoxyethylene sorbitan ester,
wherein said liposomal particles have an average diameter of from 0.5 to 3 microns,
wherein said mixture of essential plant oils comprises oils of oregano, thyme, eucalyptus, lime, frankincense, peppermint, lemon, ginger, sage, and lavender,
wherein the liposomal particle essential oil-in-water emulsion is substantially free of proteins.

2. The method of claim 1, wherein the subject is in need of treatment for a respiratory system infection.

3. The method of claim 1, wherein the liposomal composition contains liposomal particles contains the polyoxyethylene sorbitan ester in an amount ranging from 1 to 1.6 vol. % based on a total volume of the liposomal particle essential oil-in-water emulsion and a mixture of essential plant oils in an amount ranging from 1 to 2 vol. % based on a total volume of the liposomal particle essential oil-in-water emulsion.

* * * * *